United States Patent [19]

Baer

[11] Patent Number: 4,572,375

[45] Date of Patent: Feb. 25, 1986

[54] CONTAINER FOR DISPERSANT

[76] Inventor: Carl D. Baer, 3516 Nanz Ave., Louisville, Ky. 40207

[21] Appl. No.: 674,779

[22] Filed: Nov. 26, 1984

[51] Int. Cl.⁴ ............................................. A61L 9/04
[52] U.S. Cl. .............................. 206/524.1; 239/56/59; 222/325; 220/300
[58] Field of Search ............... 206/457, 524.1, 527; 239/43, 47, 56, 57, 59, 60; 220/87, 300; 222/325

[56] References Cited

U.S. PATENT DOCUMENTS

| | | | |
|---|---|---|---|
| 1,757,530 | 5/1930 | Keim | 239/57 |
| 2,642,310 | 6/1953 | Meek et al. | 239/59 |
| 2,765,194 | 10/1956 | Will | 239/60 |
| 3,292,779 | 12/1966 | Colella | 220/300 |
| 3,312,336 | 4/1967 | Fally | 220/300 |
| 3,369,691 | 2/1968 | Wei | 220/300 |
| 3,565,339 | 2/1971 | Curran | 239/60 |
| 3,727,840 | 4/1973 | Nigro | 239/43 |
| 3,848,803 | 11/1974 | Levey | 239/60 |
| 3,864,080 | 2/1975 | Valbona et al. | 239/43 |
| 4,096,994 | 6/1978 | Bryson | 239/59 |
| 4,258,874 | 3/1981 | Webinger et al. | 239/59 |
| 4,279,355 | 7/1981 | Schwartz et al. | 220/300 |
| 4,301,949 | 11/1981 | Palson et al. | 239/59 |

FOREIGN PATENT DOCUMENTS 1515260  6/1978  United Kingdom ................. 220/87

Primary Examiner—Joseph Man-Fu Moy
Assistant Examiner—David T. Fidei
Attorney, Agent, or Firm—Charles G. Lamb

[57] ABSTRACT

A container for dispersant material includes a base member and a removable cover which fits over the base member. The base member includes a reservoir mounting collar for holding a reservoir of dispersant material in place. A removable reticulated housing enclosing a dispersant material is located within the reservoir. A rotatable valved cap fits over the top of the reservoir to provide for the release of a selectable amount of dispersant.

12 Claims, 6 Drawing Figures

CONTAINER FOR DISPERSANT

BACKGROUND OF THE INVENTION

The present invention relates to dispenser containers, and more particularly to a container for a dispersant such as, for example, a room air freshener and the like.

Various types of containers for dispersants are known.

Some containers have a wick submerged in a dispersant material. The dispersant moves in the wick and, upon contact with the atmosphere, evaporates. In order to prevent evaporation when not in use, a cap is installed over the wick. This arrangement, while effective, presents a very utilitarian appearance.

Attempts have been made to enhance the asthetic appearance of a dispersant container. One such example is illustrated in U.S. Pat. No. 3,727,840, which provides a container of two hemispherical, threadably connected shells. A wick material is held in place in the bottom hemispherical shell and a dispersant is encapsulated in the top hemispherical shell by a puncturable membrane. The bottom shell also includes a projection which pierces the membrane of the top hemispherical as the shells are moved toward each other, thus, allowing dispersant to flow into the wick material. The dispersant evaporates from the wick material and exits the container through holes formed through the lower hemispherical shell. When the dispersant is used up, the entire container is disposed of.

SUMMARY OF THE INVENTION

An object of the present invention is to provide a container for a dispersant which can be refilled with a new supply of dispersant.

A further object of the present invention is to provide a refillable dispersant container which can be easily refilled with a fresh supply of dispersant.

Another object of the present invention is to provide a refillable dispersant container which holds the supply of dispersant in place within the container.

Yet a further object of the present invention is to provide a refillable dispersant container which not only securely holds the supply of dispersant in place within the container, but also provides for the installation and removal of the dispersant supply quickly and easily without the aid of tools.

An even further object of the present invention is to provide a refillable dispersant container construction of the class described which can be readily adapted to various pleasing asthetic designs.

More particularly, the present invention provides a container for a dispersant material comprising a base member, a cover member adapted to close over the base member, a generally cylindrically shaped reservoir member adapted to receive the dispersant material therein, the reservoir member having at least one slot formed in its side wall, the slot being open at the base of the reservoir member and extending from the base of the reservoir member in a generally upward and circumferential direction of the reservoir member side wall forming an acute angle between the longitudinal axis of the slot and the base of the reservoir member, reservoir locating means associated with the container base member for locating the reservoir member on the container base, and reservoir locking means adapted to be received with the at least one slot in the reservoir side wall for holding the reservoir in the location determined by the reservoir locating means.

BRIEF DESCRIPTION OF THE DRAWINGS

A more complete and thorough understanding of the present invention will be had upon reference to the following description in conjunction with the accompanying drawings in which like numerals refer to like drawings throughout and wherein.

DETAILED DESCRIPTION OF THE PREFERRED EMBODIMENT

Figure 1:
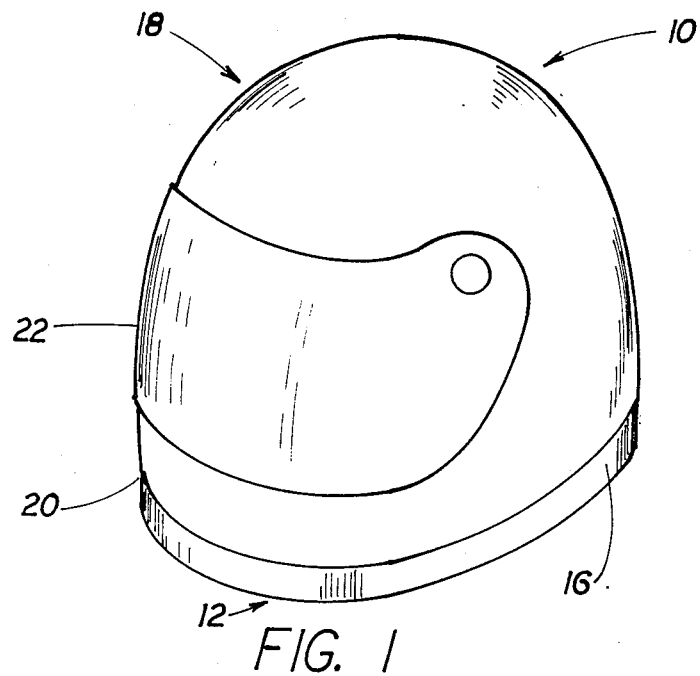
FIG. 1 is a perspective view of a cover of the container of the present invention.
Figure 2:
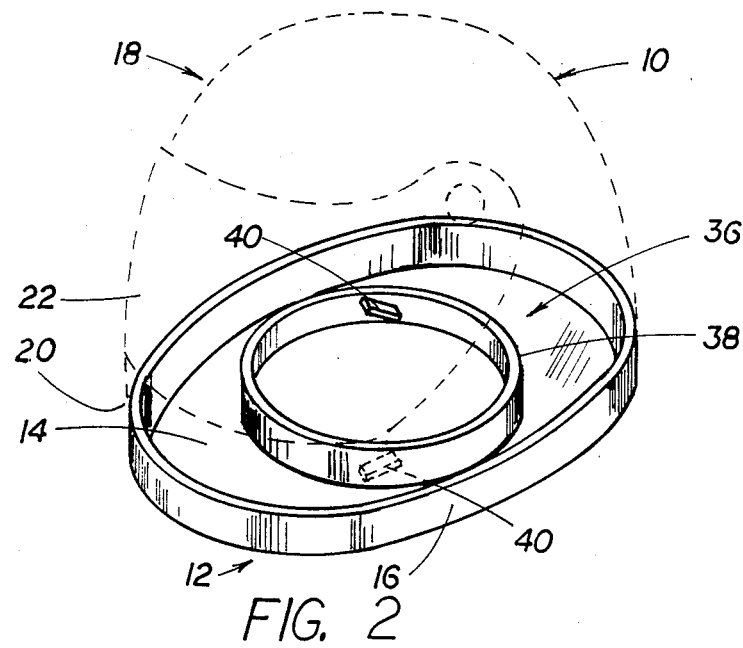
FIG. 2 is a perspective view of a base member of the container of the present invention with the container cover shown in phantom lines.

With reference to FIGS. 1 and 2, there is shown a container, generally denoted as the numeral 10 of the present invention, adapted for containing a dispersant material. Dispersant materials are, generally, those materials which are released in vapor form into an enclosure to perform a particular function. Typically, dispersant materials are used to deoderize, disinfect, control insects, and scent the confines of the enclosure, such as a room.

The container 10 includes a base member 12, which has a generally planar floor 14 and a peripheral, upstanding side wall 16 integral with the base floor 14.

The container 10 further includes a cover 18, which is adapted to removably close over the container base 12. Toward this end, the container cover 18 has an open bottom 20 of a peripheral shape corresponding to the exterior surface of the peripheral base side wall 16. The open cover bottom 20 is sized to receive the peripheral base side wall 16 in registered relationship. As shown, the container cover is in the shape of a helmet of the type used by automobile racing drivers having a movable visor 22. However, other shapes can be used for the asthetic configurations of the container covers just as well.

Figure 3:
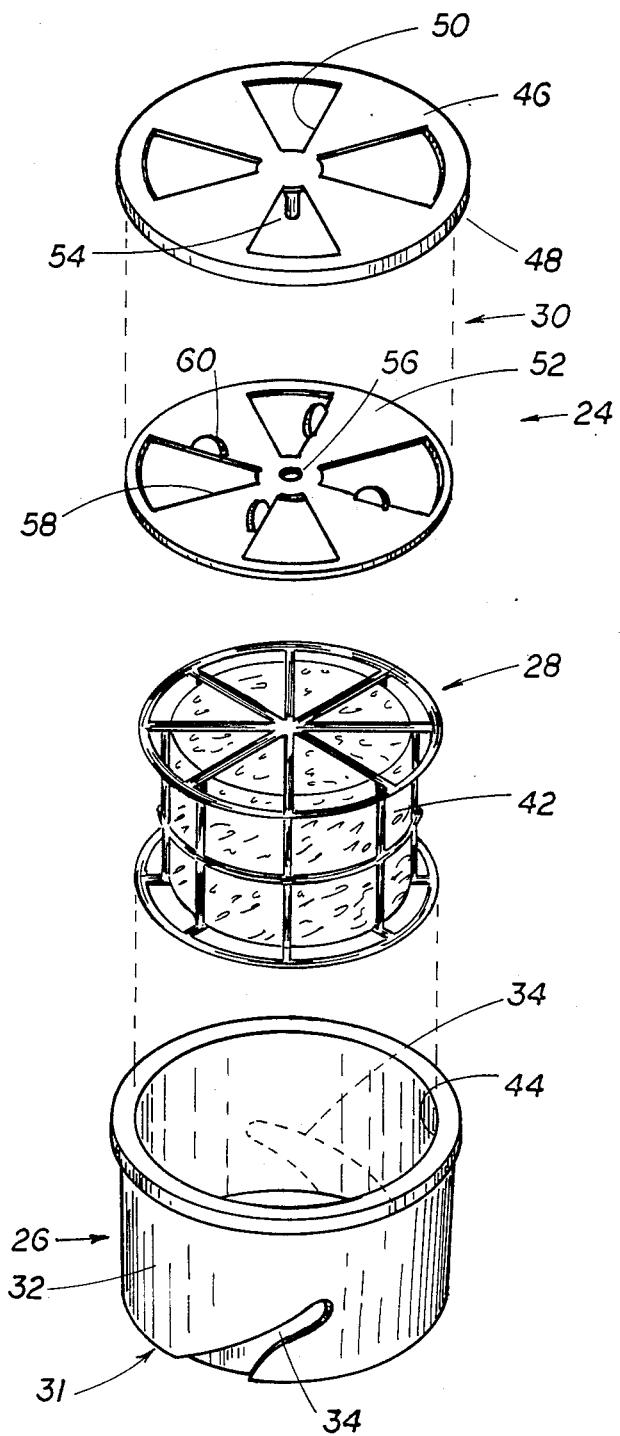
FIG. 3 is an exploded perspective view of a removable reservoir and reticulated dispersant housing of the present invention.

FIG. 3 illustrates the contents, generally denoted as the numeral 24, adapted to be removably installed within the container 10. Included are a reservoir member 26, a reticulated housing 28, and a rotatable, valved cap 30, which fits over the reservoir member 26.

The reservoir member 26 is generally cyclindrically shaped having a generally circular, planar base 31 and a sidewall 32 extending generally upwardly from the periphery of the circular base 31. Two diametrically opposed, substantially identical, blinded slots 34 are formed in the reservoir side wall 32. Each slot 34 is open at the bottom edge of the reservoir side wall 32, and extends therefrom in a generally upward, circumferential direction of the reservoir side wall 32. Thus, the longitudinal axis of each slot 30 is at an acute angle to the plane of the bottom edge of the reservoir side wall 32.

Figure 4:
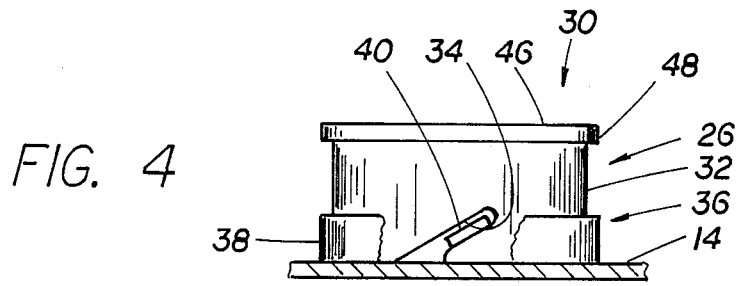
FIG. 4 is an enlarged view of a portion of the present invention illustrating the novel interconnection of the reservoir and base members.
Figure 5:
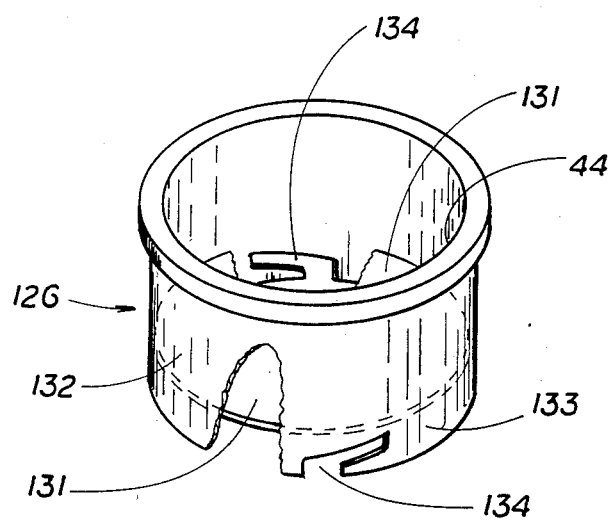
FIG. 5 is a perspective view of an alternative embodiment of a reservoir of the invention, partially broken away to more clearly show details; and, FIG. 6 is a view similar to that of FIG. 4 illustrating the novel interconnection reservoir of FIG. 5 and base members.
Figure 6:
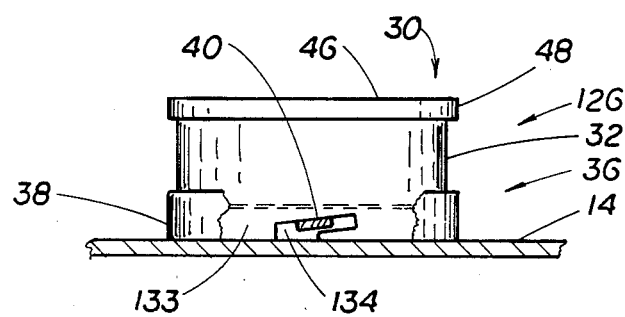

FIG. 5 and 6 illustrates an alternative embodiment of a reservoir member 126 similar to the reservoir member 26 shown in FIGS. 3 and 4. The reservoir member 126 is generally cylindrically shaped having a cylindrical side wall 132 and a circular, planar base 131 raised above or disposed a distance above the bottom circular edge of the side wall 132 to define a depending cylindrical flange 133. Two diametrically opposed, substantially identical, blind-ended slots 134 are formed through the depending flange 133 of the cylindrical side wall 132. Each slot 134 is open at the bottom circular edge of the side wall 132, and extends therefrom in a generally upward direction of the depending circular flange 133 terminating at the blind-end below the planar base 131. The longitudinal axis of each slot 134 is at an acute angle to the plane of the bottom circular edge of the side wall 132.

The present invention further provides reservoir positioning and locking means, generally denoted as the numeral 36. As shown, the positioning and locking means includes a cylindrical collar 38 extending upwardly from the container base floor 14. The inside diameter of the collar 38 is somewhat larger than the diameter of the cylindrical reservoir member 26 and is sufficient to receive the reservoir member therein in surrounding relationship thereto. The positioning and locking means further includes a pair of generally diametrically opposed, and substantially identical locking tab members 40 projecting from the cylindrical collar 38 in a generally radial upward direction of the collar 38. Each of the locking tab members 40 is in the form of an inclined ramp extending in a generally upward circumferential direction of the cylindrical collar 38. The acute angle between the inclined ramp locking tab member 40 and the container base floor 14 is substantially equal to the acute angle formed between the longitudinal axis of a slot 34 and the reservoir base 30. Each of the tab members 40 is adapted to be received in a different one of the slots 34 of the reservoir member 26.

With continued reference to FIG. 3, the reticulated housing 28 is substantially cylindrical in shape and is approximately sized to fit within the reservoir member 26. As shown, the reticulated housing 28 is formed of a network of intersecting wire-like members such that a majority of the area of the reticulated housing 28 is open. The reticulated housing 28 encloses a porous material 42, such as, for example, a sponge, which is saturated with a dispersant material. The dispersant material can be of the type which deoderizes, scents, disinfects or treats the environment to control insects upon vaporizing.

The rotatable valved cap 30 is adapted to adjustably control the rate of discharge of the dispersant material from the porous material 42. The circular cap 30 is of substantially the same diameter at the open top 44 of the reservoir member 26, and is adapted to be placed over the open reservoir top 44. The valved cap 30 is shown as including a generally circular top member 46 formed with a peripheral downwardly projecting locking lip 48 having a diameter generally equal to the diameter of the open top of the reservoir member 26. The circular member 46 is formed with a plurality of circumferentially spaced apart flow-through openings 50. The cap 30 further has rotatable, generally circular bottom member 52 coaxial with the cap top member 46, and attached to the cap top member 46 for rotation about the coaxial axis. Toward this end, an axle 54 depends from the underside of the top circular member 46 and is received in a centrally located hole 56 formed through the geometric center of the lower circular member 46. The end of the axle 54 extending through the axle receiving hole 56 can be offset or flared so that it will not slip out of the axle receiving hole 56. The circular bottom cap member 52 is also formed with a plurality of circumferentially spaced apart flow-through openings 58. The size, shape and spaced apart location of the flow-through openings 58 in the lower cap member 52 are substantially the same as the size, shape and spaced apart location of the flow-through openings 50 in the top cap member 46. The bottom cap member 52 also has upstanding flanges 60 located next to the flow-through openings 58 which project upwardly through the flow-through openings 50 of the top cap member 46. The rotatable valved cap 30 is positioned over the open top 44 of the reservoir member 26 with the top edge of the reervoir side wall 32 received within and gripped by the peripheral locking lip 48 of the top cap member 46, thus, holding the cap 30 in place. In order to adjust the flow-through open area of the cap 30, thereby controlling the rate of discharge of the dispensarate from the porous material 42 enclosed in the reservoir member 26, one need only turn the bottom cap member 52 about the axle 54 to bring the flow-through openings 58 into and out of alignment with the flow-through openings 50. This can easily be done by merely pushing against the flanges 60 of the bottom cap member 52 which project through the flow-through openings 50 of the top cap member 46 with a finger.

The reservoir member 26, 126 is installed on the container base floor 14 by placing it within the collar 38 and turning the reservoir member 26, 126 until each locking tab 40 is received in a different one of the slots 34, 134 of the reservoir side wall 32. Thus, the reservoir member 26, 126 is properly located, and locked in position. In order to remove the reservoir member 26, 126, one need only turn the reservoir member 26, 126 in the opposite direction until the locking tabs 40 are removed from the slots 34, 134.

The foregoing detailed description is given primarily for clearness of understanding and no unnecessary limitations are to be understood therefrom for modifications will become obvious to those skilled in the art upon reading this disclosure and may be made without departing from the spirit of the invention and scope of the appended claims.

What is claimed is:

1. A container for a dispersant material, comprising:
   a base member;
   a cover member having a movable visor therein, said cover member adapted to close over and engage the periphery of the base member;
   a generally cylindrically shaped reservoir member adapted to receive therein the dispersant material, the reservoir member having at least one slot formed in its side wall, the slot being open at the base of the reservoir member and extending from the base of the reservoir member in a generally upward and circumferential direction of the reservoir member side wall forming an acute angle between the longitudinal axis of the slot and the base of the reservoir member;
   reservoir locating means associated with the container base member for locating the reservoir member on the container base;

reservoir locking means adapted to be received within the at least one slot in the reservoir side wall for holding the reservoir in the location determined by the reservoir locating means;

a reticulated housing adapted to be removably received by the reservoir member; and, a porous material saturated with dispersant enclosed within the reticulated housing.

2. The container of claim 1, wherein the reservoir locking means comprises at least one tab member associated with the locating means.

3. The container of claim 2, wherein the at least one tab member comprises an inclined ramp extending at an acute angle to the container base floor substantially equal to the acute angle formed between the at least one slot in the reservoir side wall and the base of the reservoir member.

4. The container of claim 3 wherein:

the reservoir locking means comprises two diametrically opposed inclined ramps; and, the reservoir member is formed with two diametrically opposed slots.

5. The container of claim 1, wherein the reservoir locating means comprises a generally circular collar associated with the container base adapted to receive the reservoir member therein in surrounding relationship thereto.

6. The container of claim 5, wherein the reservoir locking means comprises at least one tab associated with the collar and projecting generally radially inwardly of the collar.

7. The container of claim 6, wherein the at least one tab member comprises an inclined ramp extending in a generally upward circumferential direction of the collar.

8. The container of claim 7, wherein:

the reservoir locking means comprises two diametrically opposed inclined ramps; and the reservoir member is formed with two diametrically opposed slots.

9. The container of claim 1, wherein:

the container base includes a generally planar floor, and a peripheral upstanding base side wall; and, the container cover includes an open bottom of a peripheral shape corresponding to the shape of the peripheral base side wall and sized to receive the peripheral base side wall therein.

10. The container of claim 1, further comprising a valved cap removably attached to the reservoir member over the open top thereof, the valved top being adjustable to provide for a controlled rate of discharge of dispersant.

11. The container of claim 10, wherein the valved cap comprises:

a first circular member adapted to be attached to the top edge of the reservoir member defining the top opening into the reservoir member, the first circular member being formed with a plurality of circumferentially spaced apart flow-through openings; and, a second circular member in coaxial relationship to the first circular member, the second circular member being rotatably attached to the first circular member for rotation relative thereto about the coaxial axis, and the second circular member being formed with a plurality of circumferentially spaced apart flow-through openings which move into and out of registration with the flow-through openings of the first circular member as the second circular member is rotated.

12. The container of claim 1, wherein the reservoir member comprises:

a generally cylindrically shaped side wall, and a generally circular shaped, planar base disposed a distance above the bottom circular edge of the side wall defining a depending flange; and, the at least one slot being formed through the depending cylindrical flange, the at least one slot being open to the bottom circular edge of the side wall and terminating at blind-end below the planar base.

* * * * *